US009435732B2

(12) United States Patent
Rozenboim et al.

(10) Patent No.: US 9,435,732 B2
(45) Date of Patent: Sep. 6, 2016

(54) HYPERSPECTRAL IDENTIFICATION OF EGG FERTILITY AND GENDER

(75) Inventors: Israel Rozenboim, Mazkeret Batya (IL); Eyal Ben Dor, Rishion Lezion (IL)

(73) Assignees: Yissum Research Development of the Hebrew University of Jerusalem Ltd., Jerusalem (IL); Ramot at Tel Aviv University Ltd., Tel Aviv (IL)

( * ) Notice: Subject to any disclaimer, the term of this patent is extended or adjusted under 35 U.S.C. 154(b) by 874 days.

(21) Appl. No.: 13/379,443

(22) PCT Filed: Jun. 27, 2010

(86) PCT No.: PCT/IL2010/000512
§ 371 (c)(1),
(2), (4) Date: Oct. 31, 2012

(87) PCT Pub. No.: WO2010/150265
PCT Pub. Date: Dec. 29, 2010

(65) Prior Publication Data
US 2013/0044210 A1    Feb. 21, 2013

Related U.S. Application Data

(60) Provisional application No. 61/220,211, filed on Jun. 25, 2009.

(51) Int. Cl.
*H04N 9/47*    (2006.01)
*G01N 21/31*    (2006.01)
*G01N 33/08*    (2006.01)
*G01N 21/3563*    (2014.01)

(52) U.S. Cl.
CPC .............. *G01N 21/31* (2013.01); *G01N 33/08* (2013.01); *G01N 21/3563* (2013.01); *G01N 2021/3155* (2013.01); *G01N 2201/1296* (2013.01)

(58) Field of Classification Search
CPC ........................................................ H04N 7/18
USPC ........................................................ 348/135
See application file for complete search history.

(56) References Cited

U.S. PATENT DOCUMENTS

| 3,704,144 A | 11/1972 | Arthur |
| 4,161,366 A | 7/1979 | Bol et al. |
| 4,182,571 A | 1/1980 | Furuta et al. |
| 4,603,772 A * | 8/1986 | Tomosue .................. 198/418.6 |
| 4,698,616 A * | 10/1987 | Krohn et al. .................. 341/13 |

(Continued)

FOREIGN PATENT DOCUMENTS

CN    101059425    10/2007

OTHER PUBLICATIONS

Das, K. et al. "Detecting Fertility of hatching eggs using machine vision II: neural network classifiers", Transactions of the America Society of Agricultural Engineers 1992—Nov.-Dec., vol. 35, No. 6, Nov. 1992, pp. 2035-2041.

(Continued)

*Primary Examiner* — Leron Beck
(74) *Attorney, Agent, or Firm* — A.C. Entis-IP Ltd.

(57) ABSTRACT

A hyperspectral method for detecting the present condition of an avian egg is disclosed in which a neural network algorithm is used to compare the spectrum of a test egg against a spectral library. The method can detect fertility with greater than 90% reliability on the day of laying and the gender of the chick with greater than 75% reliability on the 12th day after laying.

16 Claims, 6 Drawing Sheets

(56) References Cited

U.S. PATENT DOCUMENTS

| | | | |
|---|---|---|---|
| 4,788,427 A | 11/1988 | LeRoy | |
| 4,914,672 A | 4/1990 | Hebrank | |
| 4,955,728 A | 9/1990 | Hebrank | |
| 5,046,116 A * | 9/1991 | Melen | 382/228 |
| 5,173,737 A * | 12/1992 | Mitchell et al. | 356/53 |
| 5,344,023 A * | 9/1994 | Cox et al. | 206/508 |
| 5,504,572 A * | 4/1996 | Taylor et al. | 356/53 |
| 5,648,468 A * | 7/1997 | Spaulding | 530/359 |
| 5,679,514 A * | 10/1997 | Baker | 435/6.11 |
| 5,745,228 A * | 4/1998 | Hebrank et al. | 356/53 |
| 5,860,528 A * | 1/1999 | Emery | 206/521.1 |
| 5,865,142 A * | 2/1999 | Chang | 119/318 |
| 6,029,080 A * | 2/2000 | Reynnells et al. | 600/407 |
| 6,244,214 B1 * | 6/2001 | Hebrank | 119/6.8 |
| 6,365,339 B1 * | 4/2002 | Daum et al. | 435/4 |
| 6,373,560 B1 * | 4/2002 | Roux | 356/58 |
| 6,396,938 B1 * | 5/2002 | Tao et al. | 382/110 |
| 6,506,570 B1 * | 1/2003 | Phelps | 435/7.21 |
| 6,512,839 B1 * | 1/2003 | Toelken | 382/110 |
| 6,535,277 B2 * | 3/2003 | Chalker et al. | 356/53 |
| 6,624,787 B2 * | 9/2003 | Puzella et al. | 343/700 MS |
| 6,750,954 B2 | 6/2004 | Hebrank et al. | |
| 6,805,244 B1 * | 10/2004 | Toelken | 209/510 |
| 6,860,225 B2 | 3/2005 | Hebrank | |
| 7,019,821 B2 * | 3/2006 | Kageyama et al. | 356/53 |
| 7,154,594 B2 | 12/2006 | Reeves et al. | |
| 7,167,579 B2 * | 1/2007 | Taniguchi | 382/110 |
| 7,261,860 B1 * | 8/2007 | Vellinger et al. | 422/72 |
| 7,289,196 B2 | 10/2007 | Reeves et al. | |
| 7,336,348 B2 | 2/2008 | Reeves et al. | |
| 7,481,179 B2 * | 1/2009 | Cantrell et al. | 119/6.8 |
| 7,734,097 B1 * | 6/2010 | Porikli et al. | 382/190 |
| 7,950,349 B1 * | 5/2011 | Rollins | 119/6.8 |
| 8,364,247 B2 | 1/2013 | Opitz et al. | |
| 2001/0047771 A1 * | 12/2001 | Bulanda et al. | 119/712 |
| 2002/0157613 A1 * | 10/2002 | Phelps et al. | 119/6.8 |
| 2003/0172392 A1 * | 9/2003 | Mendu et al. | 800/19 |
| 2004/0102882 A1 * | 5/2004 | Sala et al. | 701/45 |
| 2006/0082759 A1 * | 4/2006 | Hebrank | 356/53 |
| 2006/0160080 A1 * | 7/2006 | Clinton | 435/6 |
| 2008/0097174 A1 * | 4/2008 | Maynard et al. | 600/316 |
| 2011/0204049 A1 * | 8/2011 | Weder et al. | 220/4.24 |
| 2012/0058052 A1 * | 3/2012 | Decuypere et al. | 424/9.6 |
| 2012/0084873 A1 * | 4/2012 | Sinclair et al. | 800/19 |

OTHER PUBLICATIONS

Giunchi, A., et al., "Non-Destructive freshness assessment of shell eggs using FT-NIR spectroscopy", Journal of Food Engineering, Barking, Essex, GB, vol. 89, No. 2, Nov. 1, 2008, pp. 142-148.

Lawrence, K.C., et al., "Egg embryo development detection with hyperspectral imaging", Proceedings of the SPie—The International Society for optical Engineering Spie—The International Society for Optical Engineering USA, vol. 6381, 2006, pp. 63810T-1.

Smith, D.P., et al., "Fertility and embryo development of broiler hatching eggs evaluated with hyperspectral imaging and predictive modeling system", International Journal of Poultry Science, vol. 7, No. 10, 2008, pp. 1001-1004.

Wang et al., "Generalisation Performance of Artificail Neural Networks for Near Infrared Spectral Analysis", Biosystems Engineering, Academic Press, UK, vol. 94, No. 1, May 1, 2006, pp. 7-18.

Office Action dated Apr. 24, 2014 for corresponding European application No. 10747080.9.

Office Action dated Mar. 13, 2014 for corresponding Chinese application No. 201080028138.2.

Office Action dated Mar. 3, 2014 for corresponding Eurasian application No. 201290006/13.

Office Action dated Sep. 12, 2014 for corresponding Chinese application No. 201080028138.2.

Soh, Andrew; Practical assessment of viability and growth of growth of embryos via carbon dioxide production in Japanese quail Eggs, Avian and Poultry Biology Reviews 2005, 16, pp. 194-195.

* cited by examiner

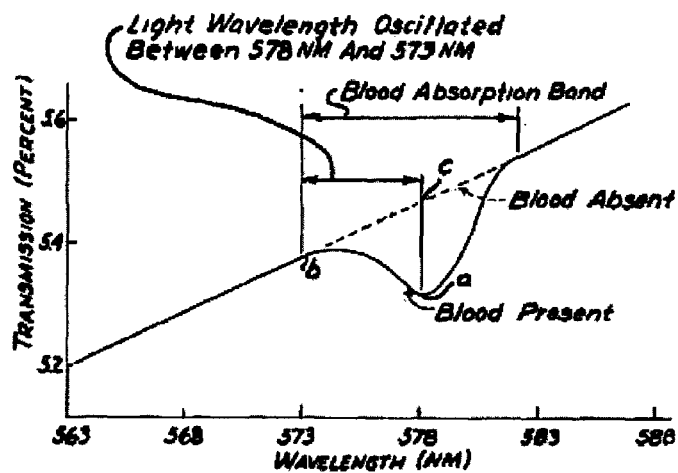
FIG. 1A
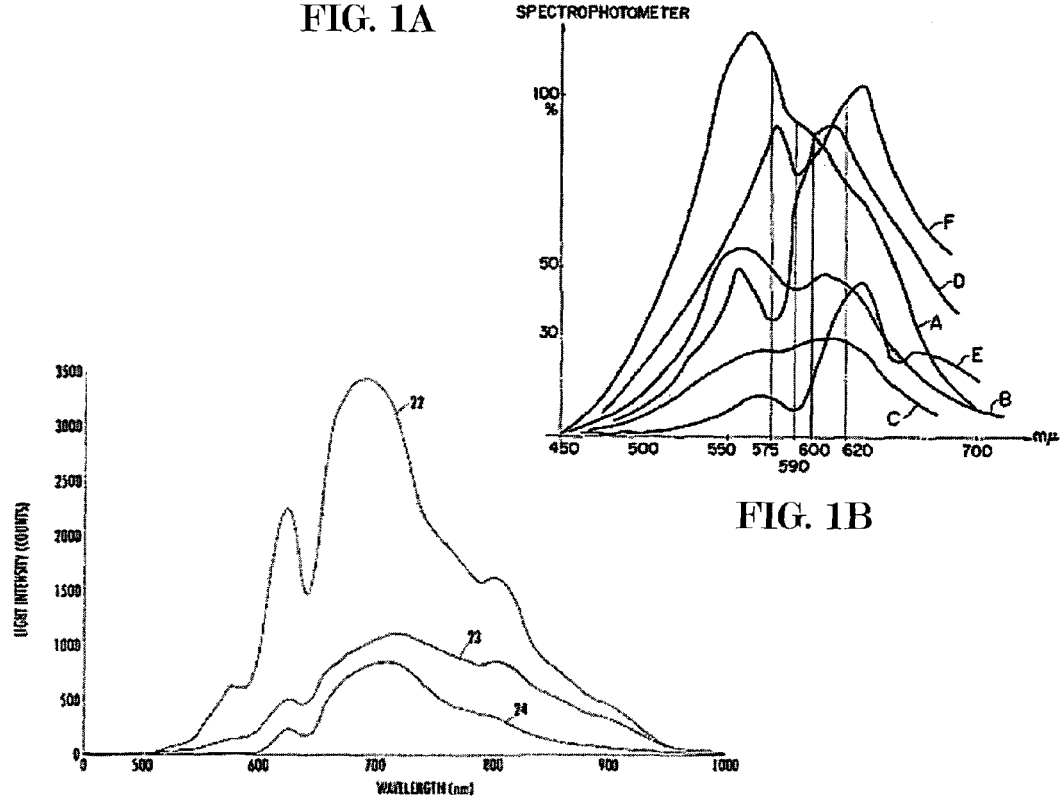
FIG. 1B
FIG. 1C
FIG. 1
(prior art)

HYPERSPECTRAL IDENTIFICATION OF EGG FERTILITY AND GENDER

RELATED APPLICATION

This application corresponds to PCT/IL2010/000512, filed Jun. 27, 2010, which claims priority from U.S. Provisional Patent Application No. 61/220,211, filed Jun. 25, 2009, the disclosures of which are incorporated herein by reference in their entirety.

FIELD OF THE INVENTION

This invention concerns non-invasive methods for determining the fertility and gender of an unhatched avian egg, in particular, the use of reflectance spectroscopy in such determinations.

BACKGROUND

Approximately 6.5 billion eggs are produced annually in the United States alone. In an industry of this size, efficient quality control and means for limiting production costs are vital. For example, a significant number (typically 10-40%) of the eggs in a given hatchery are infertile. These eggs consume space and energy within the incubator, and can also cause contamination of other eggs. Analogous inefficiencies are caused by the difficulty that while 50% of the fertilized eggs contain male chicks, which are obviously useless to a hatchery that is dedicated to raising egg-laying hens, the determination of the sex of the chick is normally not performed until the chick is hatched, at which point, male chicks are disposed of. In addition to the energy costs of incubating a useless egg to maturity, there is the problem of eliminating the male chicks after hatching. To this end, a number of non-invasive techniques have been developed for assessing the fertility and gender of unhatched avian eggs.

For example, Soh (*Avian and Poultry Biology Reviews* 2005, 16, 194-195) has shown that it is possible in principle to detect a fertile egg by the $CO_2$ that is given off by the chick inside. This method suffers from the drawback that a measurement for a single egg will take on the order of 15 minutes, far too long for a commercial hatchery. MRI has been proposed as an in ovo method for sex determination; a device based on this principle was disclosed in U.S. Pat. No. 6,029,080. As with $CO_2$ detection, the primary drawback of MRI (in addition to the high cost of the necessary equipment) is the unduly long time (ca. 5 min per egg) required to obtain a usable image.

Methods based on measuring the amount of light transmitted by an egg (in essence, automated versions of traditional egg-candling methods) are well-known in the art; see, for example, the inventions disclosed in U.S. Pat. Nos. 5,745,228, 6,373,560, 6,750,954, and 7,019,821. More sophisticated methods that measure modulation of a light signal passing through an egg due to motion (e.g. the beating heart of the developing chick) within have been disclosed in, for example, U.S. Pat. Nos. 5,173,737, 6,860,225, 7,154,594, 7,289,196, and 7,336,348. Thermographic methods that measure infrared light emitted by a live egg have served as the basis for inventions disclosed in, e.g., U.S. Pat. Nos. 4,788,427, 4,914,672, and 4,955,728. The primary disadvantage of all of these methods is that they cannot provide a reliable measure of egg fertility until at least 10 days (in most cases, more) after the egg has been settled in the incubator.

Inventions have been disclosed that use optical spectroscopic methods, that is, absorption of light as a function of its wavelength, to measure egg fertility. For example, U.S. Pat. No. 3,704,144 (hereinafter '144) discloses a method of determining egg fertility by measuring the phase relationship of a frequency-modulated beam of light (the frequency oscillates around 575 nm, where blood absorbs strongly) passing through an egg with that of the same beam that has not passed through the egg. The presence of blood in the egg will lead to inversion of the phase of the light passing through the egg. U.S. Pat. No. 4,182,571 (hereinafter '571) discloses a method of determining egg fertility by measuring the egg's absorption of light at 575, 590, and 620 nm; absorption at 575 nm is associated with blood in a fertile egg, 620 nm with an addled egg, and the absorption at 590 nm is used to calibrate the other two measurements. Typical results of these methods are shown in FIGS. 1A and 1B, respectively. The primary disadvantage of these methods is that blood does not form until about two days after the egg is settled in the incubator, so they cannot be used even in principle during the first day or two after the egg is settled in the incubator (in practice, it is unlikely that they are sufficiently sensitive to detect fertility for at least several days more). Furthermore, since they are designed to detect blood, they cannot be used for detection of gender.

U.S. Pat. No. 6,535,277 discloses a reflectance spectroscopy method for determining egg fertility. According to this method, an egg is illuminated with a continuum of light extending from 300 nm to 1100 nm, and the reflectance spectrum obtained then compared with known spectra of fertile and infertile eggs. FIG. 1C shows typical results of this method. Because this method is only able to measure gross spectral changes, it, like those disclosed in '144 and '571, is relatively insensitive, and hence cannot detect the gender of the developing chick.

A multivariate analysis method was developed by Lawrence et al. (Lawrence, K. C.; Smith, D. P.; Windham, W. R.; Heitschmidt, G. W.; Park, B. "Egg Embryo Development Detection with Hyperspectral Imaging." *Poultry Science* 2006, 5, 964) for detection of egg fertility. Their method is also incapable of monitoring the embryo within the first day after the egg is settled in the incubator.

Even though a fertile egg already contains 40-60,000 cells at the moment of laying, none of the non-invasive methods yet developed can detect egg fertility that early. Thus, a non-invasive in ovo method for detecting avian egg fertility on the day of laying that can also detect the gender of the chick remains a long-felt need.

SUMMARY OF THE INVENTION

The invention disclosed in the present invention uses hyperspectral analysis of an optical spectrum (in a preferred embodiment, a reflectance spectrum) obtained from an egg to be tested. In contrast to prior methods, the analysis is performed over a spectral region that includes the mid-IR (wavelengths up to about 2500 nm) in order to account for the $CaCO_3$ in the egg shell, which absorbs at 2340 nm, and to filter out the signal from the egg shell from the total spectral signal. The use in the present invention of spectra that include a wider range of wavelengths relative to the spectral ranges of analogous techniques known in the prior art provides several advantages. Since the egg shell is the primary factor inhibiting accurate detection of biochemical markers within the egg, the ability to calibrate obtained spectra for the contributions made by the shell makes the method herein disclosed significantly more sensitive than those known in the art. Prior methods tend to measure changes associated with the presence of blood in the egg, which, as described above, makes them ineffective even in principle before day 2 after the egg has been settled in the incubator. The present invention makes use of the entire spectrum, which enables detection of biological components other than blood, hence enabling both detection of fertility earlier than day 2 and detection of the gender of the chick within the egg.

Additional sensitivity is provided by use of neural network analysis. Principal component analysis (PCA) enables determination of the spectral features responsible for the variance between a control (unfertilized) egg and the one being tested, and neural network analysis based on the PCA then provides a means of detecting small but significant changes between the control and experimental eggs. The additional sensitivity of the hyperspectral measurement and analysis method herein disclosed enables determination of fertility on day zero (i.e. in a freshly-laid egg) with an accuracy of about 90%; determination of fertility on days 1 and 2 with an accuracy of greater than about 90%, and determination of gender at day 12 with an accuracy of about 80%.

It is thus one object of the present invention to disclose a non-invasive method for detecting the present condition of an avian egg, comprising the steps of (a) measuring at least one spectrum of said avian egg over at least one predetermined wavelength range; (b) using a predefined algorithm to compare said spectrum with a predefined database of spectra defining possible values of said present condition; and (c) using the results of said comparison to assess the present condition of said avian egg. It is within the essence of the invention that the method herein disclosed enables detection of fertility with <1% false positives within 24 hours after the time that said egg is settled in the incubator. This enables the extraction of non fertile eggs, without the risk of removing a fertile egg.

It is a further object of this invention to disclose such a method, wherein said database further includes a principal component analysis of said spectra.

It is a further object of this invention to disclose such a method, wherein said step of using a predefined algorithm further comprises a step of using a neural network algorithm.

It is a further object of this invention to disclose such a method, wherein said step of using a neural network algorithm comprises steps of (a) using principal component analysis to transform a data set; (b) selecting the first m scores from each sample; and (c) inputting said m scores into a neural network comprising n neurons, a transfer function in the hidden layer, and a linear transfer function for the output.

It is a further object of this invention to disclose such a method, wherein said transfer function in the hidden layer is the "tansig" function.

It is a further object of this invention to disclose such a method, wherein m=5 and n=3.

It is a further object of this invention to disclose such a method, wherein said step of using a predefined algorithm to compare said spectrum with a predefined database of spectra defining possible values of said present condition further comprises an additional step of preprocessing the spectral data.

It is a further object of this invention to disclose such a method, wherein said additional step of preprocessing the spectral data further comprises an additional step of performing dimension reduction.

It is a further object of this invention to disclose such a method, wherein said additional step of preprocessing the spectral data further comprises an additional step of performing spectral enhancement.

It is a further object of this invention to disclose such a method, wherein said step of performing spectral enhancement includes at least one step chosen from the group consisting of (a) smoothing and (b) noise reduction.

It is a further object of this invention to disclose such a method as defined in any of the above, wherein said step of measuring at least one of said avian egg further includes the additional steps of (a) obtaining a reference spectrum; (b) obtaining a test spectrum; and (c) using said reference spectrum to correct said test spectrum.

It is a further object of this invention to disclose such a method, wherein said step of obtaining a reference spectrum further comprises the additional step of constructing a reference spectrum according to a predetermined physical model.

It is a further object of this invention to disclose such a method, wherein said step of obtaining a reference spectrum further comprises the additional step of obtaining a reference spectrum by means of physical measurement.

It is a further object of this invention to disclose such a method, wherein said step of measuring at least one spectrum of said avian egg over at least one predetermined wavelength range further comprises the additional steps of: (a) obtaining a hyperspectral camera capable of recording spectra over said predetermined wavelength range; (b) placing said avian egg within the field of view of said hyperspectral camera; and (c) using said hyperspectral camera to obtain at least one spectrum of said avian egg.

It is a further object of this invention to disclose such a method, wherein said step of measuring said at least one spectrum of said avian egg over a predetermined wavelength is preceded by a step of confirming that said avian egg is within the field of view of said hyperspectral camera.

It is a further object of this invention to disclose such a method, wherein said step of confirming that said avian egg is within the field of view of said hyperspectral camera further comprises additional steps of (a) obtaining a test measurement by measuring the amount of light of at least one predetermined wavelength corresponding to an absorption feature of said avian egg reaching a predefined portion of the field of view of said hyperspectral camera; and (b) comparing said test measurement to a reference measurement at substantially the same at least one predetermined wavelength. It is within the essence of the invention wherein the presence of said avian egg within the field of view of said camera is confirmed when the results of step of comparing said test measurement to said reference measurement show a difference between the two measurements that exceeds a predetermined threshold.

It is a further object of this invention to disclose such a method, wherein said at least one predetermined wavelength is within the calcite absorption band centered at about 2340 nm.

It is a further object of this invention to disclose such a method as defined in any of the above, further comprising the additional step of placing said avian egg in a sample holder adapted for holding an avian egg during spectral analysis, said additional step occurring prior to the step of measuring at least one.

It is a further object of this invention to disclose such a method, wherein said step of placing said avian egg in a sample holder comprises the step of obtaining a sample holder comprising (a) means for excluding ambient light, (b)

means for permitting light from a light source to illuminate said egg, and (c) means for permitting at least a portion of the light reflected from said egg to impinge on a detector.

It is a further object of this invention to disclose such a method, wherein said step of placing said avian egg in a sample holder comprises the step of obtaining a sample holder comprising (a) a casing; (b) two substantially parallel rods rotatably mounted within said casing and arranged to support an avian egg placed thereupon; (c) at least one motor in mechanical connection with said rods, said at least one motor adapted to rotate each of said rods about its longitudinal axis; (d) light admitting means for admitting light emitted by a light source into said casing, said light admitting means disposed such that at least a portion of said light illuminates an avian egg placed upon said rods; and (e) means for admitting one end of a fiber optic cable into said casing such that at least a portion of said light admitted via said light admitting means and reflected from said avian egg enters said fiber optic cable.

It is a further object of this invention to disclose such a method, wherein said sample holder is made of soft material.

It is a further object of this invention to disclose such a method, wherein said sample holder is black.

It is a further object of this invention to disclose such a method, wherein at least part of the interior surface of said sample holder is black.

It is a further object of this invention to disclose such a method as defined in any of the above, wherein said present condition is chosen from the group consisting of (a) fertility; (b) gender; (c) both of the above.

It is a further object of this invention to disclose such a method, wherein said present condition is fertility, and further wherein said determination is made not more than 48 hours after the time that said egg is settled in the incubator.

It is a further object of this invention to disclose such a method, wherein said present condition is fertility, and further wherein said determination is made not more than 24 hours after the time that said egg is settled in the incubator.

It is a further object of this invention to disclose such a method, wherein said present condition is gender, and further wherein said determination is made not more than two weeks after the time said egg is settled in the incubator.

It is a further object of this invention to disclose such a method, wherein said present condition is gender, and further wherein said determination is made on the twelfth day after the egg is settled in the incubator.

It is a further object of this invention to disclose such a method as defined in any of the above, wherein said spectrum is a reflectance spectrum.

It is a further object of this invention to disclose such a method, wherein said reflectance spectrum is obtained by illuminating said egg substantially along its longitudinal axis and measuring the intensity of light impinging on a detector, said detector positioned so as to detect light emanating from said egg at an angle of greater than about 10° and less than about 90° relative to said longitudinal axis.

It is a further object of this invention to disclose such a method as defined in any of the above, wherein said spectrum is a transmittance spectrum.

It is a further object of this invention to disclose such a method as defined in any of the above, wherein said spectrum extends from the near-UV to the mid-IR.

It is a further object of this invention to disclose such a method as defined in any of the above, wherein said spectrum extends from about 300 nm to about 2500 nm.

It is a further object of this invention to disclose such a method as defined in any of the above, wherein said spectrum is a derivative spectrum.

It is a further object of this invention to disclose such a method as defined in any of the above, further including a step of providing a temperature-controlled environment in which said step of measuring said spectrum is performed.

It is a further object of this invention to disclose such a method, wherein said step of providing a temperature-controlled environment in which said step of measuring said spectrum is performed further comprises a step of providing active temperature control to said environment.

It is a further object of this invention to disclose such a method, wherein said step of providing a temperature-controlled environment in which said step of measuring said spectrum is performed further comprises a step of providing passive temperature control to said environment.

It is a further object of this invention to disclose such a method as defined in any of the above, wherein said step of using a predefined algorithm to compare said spectrum with a predefined database of spectra defining possible values of said present condition is preceded by a step of transferring said at least one spectrum to a computing device, and further wherein said step of using a predefined algorithm to compare said spectrum with a predefined database of spectra defining possible values of said present condition further comprises a step of using dedicated software installed on said computing device to perform said comparison.

It is a further object of this invention to disclose such a method as defined in any of the above, further including an additional step of illuminating said avian egg from a plurality of independent light sources.

It is a further object of this invention to disclose a non-invasive method of screening avian eggs, comprising the steps of (a) measuring at least one spectrum of each of a plurality of avian eggs over at least one predetermined wavelength range; (b) using a predefined algorithm to compare each of said spectra with a predefined database of spectra defining possible values of said present condition; (c) using the results of said comparison to assess the present condition of each of said avian eggs; and (d) discarding any egg for which said present condition does not match a predefined condition.

It is a further object of this invention to disclose such a method for screening avian eggs, wherein said database further includes a principal component analysis of said spectra.

It is a further object of this invention to disclose such a method for screening avian eggs, wherein said step of using a predefined algorithm further comprises a step of using a neural network algorithm.

It is a further object of this invention to disclose such a method for screening avian eggs, wherein said step of using a neural network algorithm comprises steps of (a) using principal component analysis to transform a data set; (b) selecting the first m scores from each sample; and (c) inputting said m scores into a neural network comprising n neurons, a transfer function in the hidden layer, and a linear transfer function for the output.

It is a further object of this invention to disclose such a method, wherein said transfer function in the hidden layer is the "tansig" function.

It is a further object of this invention to disclose such a method for screening avian eggs, wherein m=5 and n=3.

It is a further object of this invention to disclose such a method for screening avian eggs, wherein said step of using a predefined algorithm to compare said spectrum with a predefined database of spectra defining possible values of said present condition further comprises an additional step of preprocessing the spectral data.

It is a further object of this invention to disclose such a method for screening avian eggs, wherein said additional step of preprocessing the spectral data further comprises an additional step of performing dimension reduction.

It is a further object of this invention to disclose such a method for screening avian eggs, wherein said additional step of preprocessing the spectral data further comprises an additional step of performing spectral enhancement.

It is a further object of this invention to disclose such a method for screening avian eggs, wherein said step of performing spectral enhancement includes at least one step chosen from the group consisting of (a) smoothing and (b) noise reduction.

It is a further object of this invention to disclose such a method for screening avian eggs, further comprising the additional steps of (a) obtaining a hyperspectral camera capable of recording spectra over said predetermined wavelength range; (b) placing said avian eggs within the field of view of said hyperspectral camera; and (c) using said hyperspectral camera to obtain at least one spectrum of each of said plurality of avian eggs.

It is a further object of this invention to disclose such a method for screening avian eggs, further comprising the additional step of obtaining a plurality of fiber optic cables at least equal in number to the number of said avian eggs, wherein each of said plurality of fiber optic cables is in optical communication with one of said plurality of avian eggs, and further wherein each of said plurality of fiber optic cables is adapted to transmit at least a portion of the light reflected from an avian egg to a predetermined area within the field of view of said imaging camera.

It is a further object of this invention to disclose such a method for screening avian eggs, wherein said step of measuring at least one spectrum of each of a plurality of avian eggs over at least one predetermined wavelength range further comprises additional steps of (a) obtaining at least one reference spectrum; (b) obtaining at least one test spectrum; and (c) using said at least one reference spectrum to correct said at least one test spectrum.

It is a further object of this invention to disclose such a method for screening avian eggs, wherein said step of measuring at least measuring at least one spectrum of each of a plurality of avian eggs over at least one predetermined wavelength range further comprises additional steps of (a) obtaining at least one calibration spectrum; and (b) using said at least one calibration spectrum to calibrate at least one spectral feature.

It is a further object of this invention to disclose such a method for screening avian eggs, further comprising the additional steps of (a) obtaining at least one reference spectrum; (b) obtaining at least one calibration spectrum; (c) obtaining at least one test spectrum; (d) using said at least one reference spectrum to correct said at least one test spectrum; and (e) using said calibration spectrum to calibrate at least one spectral feature.

It is a further object of this invention to disclose such a method for screening avian eggs, wherein said step of measuring at least one spectrum of each of a plurality of avian eggs over at least one predetermined wavelength range is preceded by a step of confirming that each of said plurality of avian eggs is within the field of view of said hyperspectral camera.

It is a further object of this invention to disclose such a method for screening avian eggs, wherein said step of confirming that each of said plurality of avian eggs is within the field of view of said hyperspectral camera further comprises additional steps of (a) obtaining a test measurement by measuring the amount of light of at least one predetermined wavelength corresponding to an absorption feature of said avian egg reaching a predefined portion of the field of view of said hyperspectral camera; and (b) comparing said test measurement to a reference measurement at substantially the same at least one predetermined wavelength. It is within the essence of the invention wherein the presence of an avian egg within the field of view of said camera is confirmed when the results of step of comparing said test measurement to said reference measurement show a difference between the two measurements that exceeds a predetermined threshold.

It is a further object of this invention to disclose such a method for screening avian eggs, wherein said at least one predetermined wavelength is within the calcite absorption band centered at about 2340 nm.

It is a further object of this invention to disclose such a method for screening avian eggs, wherein said present condition is chosen from the group consisting of (a) fertility; (b) gender; (c) both of the above.

It is a further object of this invention to disclose such a method for screening avian eggs, wherein said present condition is fertility, and further wherein said determination is made not more than 48 hours after the time that said egg is settled in the incubator.

It is a further object of this invention to disclose such a method for screening avian eggs, wherein said present condition is fertility, and further wherein said determination is made not more than 24 hours after the time that said egg is settled in the incubator.

It is a further object of this invention to disclose such a method for screening avian eggs, wherein said present condition is gender, and further wherein said determination is made not more than two weeks after the time said egg is settled in the incubator.

It is a further object of this invention to disclose such a method for screening avian eggs, wherein said present condition is gender, and further wherein said determination is made on the twelfth day after the egg is settled in the incubator.

It is a further object of this invention to disclose such a method for screening avian eggs, wherein said spectrum is a reflectance spectrum.

It is a further object of this invention to disclose such a method for screening avian eggs, wherein said reflectance spectrum is obtained by illuminating said egg substantially along its longitudinal axis and measuring the intensity of light impinging on a detector, said detector positioned so as to detect light emanating from said egg at an angle of greater than about 10° and less than about 90° relative to said longitudinal axis.

It is a further object of this invention to disclose such a method for screening avian eggs, wherein said spectrum is a transmittance spectrum.

It is a further object of this invention to disclose such a method for screening avian eggs, wherein said spectrum extends from the near-UV to the mid-IR.

It is a further object of this invention to disclose such a method for screening avian eggs, wherein said spectrum extends from about 300 nm to about 2500 nm.

It is a further object of this invention to disclose such a method for screening avian eggs, wherein said spectrum is a derivative spectrum.

It is a further object of this invention to disclose such a method for screening avian eggs, further including a step of providing a temperature-controlled environment in which said step of measuring said spectrum is performed.

It is a further object of this invention to disclose such a method for screening avian eggs, wherein said step of providing a temperature-controlled environment in which said step of measuring said spectrum is performed further comprises a step of providing active temperature control to said environment.

It is a further object of this invention to disclose such a method for screening avian eggs, wherein said step of providing a temperature-controlled environment in which said step of measuring said spectrum is performed further comprises a step of providing passive temperature control to said environment.

It is a further object of this invention to disclose such a method for screening avian eggs, wherein said step of using a predefined algorithm to compare said spectrum with a predefined database of spectra defining possible values of said present condition is preceded by a step of transferring said at least one spectrum to a computing device, and further wherein said step of using a predefined algorithm to compare said spectrum with a predefined database of spectra defining possible values of said present condition further comprises a step of using dedicated software installed on said computing device to perform said comparison.

It is a further object of this invention to disclose such a method for screening avian eggs, further including an additional step of illuminating said avian egg from a plurality of independent light sources.

It is a further object of this invention to disclose a sample holder for collecting a spectrum of an avian egg, said sample holder comprising (a) an outer casing; (b) an inner casing that defines a test volume; (c) means for introducing at least one fiber optic cable into the interior of said sample holder; and (d) means for separating at least part of the upper portion of said sample holder from the lower portion of said sample holder. It is within the essence of the invention wherein said sample holder is adapted to exclude ambient light during said collection of said spectrum.

It is a further object of this invention to disclose such a sample holder, wherein said inner casing defines a test volume that is substantially ovoid in shape.

It is a further object of this invention to disclose such a sample holder, wherein at least a portion of the surface of said inner casing that contacts said egg is made of a soft material.

It is a further object of this invention to disclose such a sample holder, wherein said means for introducing at least one fiber optic cable into the interior of said sample holder comprises a passageway interconnecting said volume defined by said inner casing with the exterior environment.

It is a further object of this invention to disclose such a sample holder, wherein the diameter of said passageway is adapted for introducing at least one fiber optic cable.

It is a further object of this invention to disclose such a sample holder, wherein said means for introducing at least one fiber optic cable into the interior of said sample holder further comprises a guide tube of inner diameter adapted for passage of at least one fiber optic cable, said guide tube in optical connection with said passageway.

It is a further object of this invention to disclose such a sample holder, wherein said means for separating at least part of the upper portion of said sample holder from the lower portion of said sample holder comprise a hinge.

It is a further object of this invention to disclose such a sample holder, wherein said upper portion of said sample holder comprises a lid adapted to fit snugly against said lower portion.

It is a further object of this invention to disclose such a sample holder, further comprising a base adapted to allow said sample holder to sit stably on a flat surface.

It is a further object of this invention to disclose a sample holder for collecting a spectrum of an avian egg, said sample holder comprising (a) a casing; (b) two substantially parallel rods rotatably mounted within said casing and arranged to support an avian egg placed thereupon; (c) at least one motor in mechanical connection with said rods, said at least one motor adapted to rotate each of said rods about its longitudinal axis; (d) light admitting means for admitting light emitted by a light source into said casing, said light admitting means disposed such that at least a portion of said light illuminates an avian egg placed upon said rods; and (e) means for admitting one end of a fiber optic cable into said casing such that at least a portion of said light admitted via said light admitting means and reflected from said avian egg enters said fiber optic cable. It is within the essence of the invention wherein rotation of said avian egg enables collection of spectral data from the entire circumference of said avian egg.

It is a further object of this invention to disclose such a sample holder, wherein the distance between the end of said fiber optic cable located within said casing and said avian egg is between 2 cm and 10 cm.

It is a further object of this invention to disclose an apparatus for non-invasively determining the present condition of at least one avian egg, said apparatus comprising (a) a sample holder according to any of the above; (b) spectrometer means adapted for obtaining at least one spectrum of an avian egg placed within said sample holder; (c) data transfer means for transferring said at least one spectrum to a computing device; and (d) computing means installed on said computing device, adapted to analyze said at least one spectrum according to a predetermined algorithm.

It is a further object of this invention to disclose such an apparatus, further comprising a database of database of spectra defining possible values of said present condition, wherein said database is installed on said computing device.

It is a further object of this invention to disclose such an apparatus, wherein said predefined algorithm comprises a neural network algorithm.

It is a further object of this invention to disclose such an apparatus, wherein said neural network algorithm comprises (a) means for performing a principal component analysis to transform a data set; (b) means for selecting the first m scores from each sample; and (c) means for inputting said m scores into a neural network comprising n neurons, a transfer function in the hidden layer, and a linear transfer function for the output.

It is a further object of this invention to disclose such an apparatus, wherein said transfer function in the hidden layer is the "tansig" function.

It is a further object of this invention to disclose such an apparatus, wherein m=5 and n=3.

BRIEF DESCRIPTION OF THE FIGURES

The invention herein disclosed is described with reference to the figures, wherein FIG. 1 shows sample spectra from methods known in the art for testing avian eggs;

DETAILED DESCRIPTION OF THE INVENTION

Figure 2:
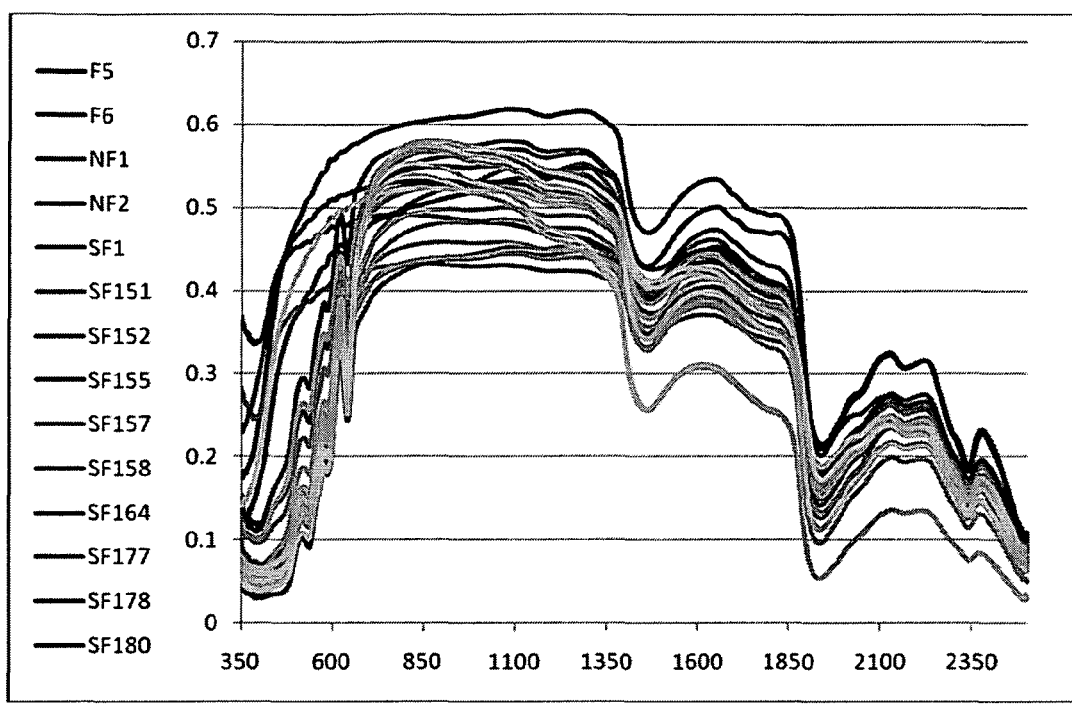
FIG. 2 shows sample reflectance spectra for a plurality of types of eggs obtained by the method disclosed in the present invention.

The present invention is described hereinafter with reference to the drawings and examples, in which preferred embodiments are described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

As used herein, the term "spectrum" refers to any measurement in which electromagnetic radiation impinges on a target and the intensity of the electromagnetic radiation as a function of its wavelength is recorded subsequent to the interaction of the electromagnetic radiation with the target. The term "reflectance spectrum" specifically refers to a spectrum in which the detector is placed in such a manner as to measure light that emerges from the target at an angle less than about 90° relative to the incident light.

In the method disclosed herein, a spectrum of the avian egg to be tested is measured. In a preferred embodiment of the invention, the spectrum is measured from the near-UV to the mid-IR. In a most preferred embodiment of the invention, the spectrum is measured from about 300 nm to about 2500 nm. In preferred embodiments of the invention, the spectrum is measured in reflectance mode, in which the detector is placed less than 90° relative to the incident light. Spectra can be measured using any commercial spectrometer capable of producing a spectrum over the desired wavelength range and in reflectance mode. In one embodiment of the invention, the spectral analysis is performed using the original reflectance units (R). In a preferred embodiment of the invention, the spectral analysis is performed by using any or all of the following: (a) the relationship $A=\log(1/R)$, (b) $dR/d\lambda$ or $dA/d\lambda$ (or numerical approximations thereof), where $\lambda$ is the wavelength, and (c) $R-R_{ref}$, where $R_{ref}$ is the reflectance of an eggshell itself as determined in a separate measurement. In other embodiments of the invention, derivative spectra are used in order that true spectral features can be more easily identified.

In preferred embodiments of the invention, the spectrum of the egg is obtained in conjunction with a reference spectrum to correct for atmospheric absorbances, non-linearities in the detector, etc. The reference spectrum can be obtained by any of the usual methods known in the art for measuring background or reference spectra, or, in some embodiments of the invention, is obtained by calculation from an appropriate model.

The spectral data are transferred to a computing device for analysis; the computing device may be located within the spectrometer, or it may be an external computer. In some embodiments of the invention, conversion of raw data to a spectrum (reflectance, transmittance, or absorbance) is performed using the software installed in the spectrometer, and the spectrum rather than the raw data is then transferred to a computing device. The spectra are then analyzed for markers that represent the condition of the egg (e.g. whether or not it is fertile, or, for a fertile egg, whether the embryo or chick therein is male or female). The analysis may be performed according to any protocol known in the art that is capable of isolating the markers of interest from the background. In a preferred embodiment of the invention, a neural network algorithm is used, as described in detail below.

In some embodiments of the invention, the method further includes additional steps of data correction or analysis. As described above, in some embodiments of the invention, derivative spectra are used. In addition to background correction, other forms of preprocessing prior to use of the neural network algorithm are possible, e.g. noise reduction, spectral enhancement, smoothing, etc., according to any method known in the art. In some embodiments, in order to increase the efficiency of the calculation, dimensional reduction is performed in order to reduce the amount of data entered into the neural network.

These methods also make possible a non-invasive method for screening a plurality of avian eggs. Spectra are obtained for a plurality of eggs, and the above methods are used to determine the present condition (e.g. fertility or gender) of the egg. Those eggs for which the present condition is not the desired condition (e.g. infertile if fertile eggs are desired) are then discarded.

Reference is now made to FIG. 2, which presents typical spectra of a number of different types of chicken eggs taken according to the method disclosed in the present invention. These spectra show numerous bands that appear to indicate variations in the biochemical properties of the content of the eggs. Spectra such as these are used to build a spectral library comprising eggs in known states (fertile or infertile; male or female) from a variety of types of birds. In a preferred embodiment of the invention, each spectrum represents the average of a plurality of measurements. After the library spectra have been obtained, they undergo a Principal Component Analysis (PCA) and are used as a "training set" for a neural network algorithm. The PCA helps the user to discard irrelevant data by retaining only those data that have the greatest deviation from the null hypothesis, namely that at a given wavelength the spectral property of interest (e.g. reflectivity or absorbance) is identical for both fertile and infertile eggs. For training the neural network, any training algorithm known in the art may be used. In preferred embodiments, iterative methods are used to derive a best set of parameters. As a non-limiting example, the Leverberg/Marquand back propagation training function can be used beginning with random weights; if a sufficiently accurate set of parameters fails to be obtained after a predetermined number of iterations, the process is begun anew with a different starting set of random weights. In preferred embodiments of the invention, the database of information used in the training set is derived from a sample of eggs from a batch similar to or identical to the ones eventually to be tested. Each training set can then be stored for future reference. In other embodiments of the invention, the training set is retrieved from a pre-existing database. In yet other embodiments of the invention, a new training set is created for each new batch of eggs to be analyzed.

The statistical analysis is then performed by using a neural network analysis algorithm. In a most preferred embodiment, the neural network algorithm comprises three steps. In the first step, the data are transformed via a PCA. The first m scores (in a most preferred embodiment, m=5) from each sample are chosen as the input for the neural network. Finally, the neural network has n neurons (in a most preferred embodiment, n=3), with the "tansig" transfer function in the hidden layer and a "linear" transfer function for the output.

In preferred embodiments, the neural network algorithm inputs are processed in each neuron and then undergo a calculation based on a transfer function as well as a predefined weight. In a preferred embodiment of the invention, the transfer function used is "tansig," the hyperbolic tangent sigmoid transfer function. The outputs from the hidden layer after the calculation serve as the input for the output layer that combines all the neurons calculation into the final result.

The analysis of a test egg is then performed as follows: a spectrum (in a preferred embodiment, a reflectance spectrum extending from about 300 nm to about 2500 nm) of the egg to be tested is obtained. In preferred embodiments, the spectrum thus obtained is an average of a plurality n of individual measurements, where n is sufficiently large (typically about 30) to provide a noticeable improvement in the signal-to-noise ratio. The principal components of the test spectrum are then calculated using the statistical methods described above. The principal components are then compared with those of the spectra in the library, again using the neural network based software. The status of the library spectrum with the best correlation to the test spectrum (e.g. fertile or infertile; male or female) is then taken to be the status of the egg represented by the test spectrum. The strength of the correlation can be assessed by any statistical method preferred by the operator (e.g., highest R value or lowest chi-squared or SEC/SEP).

As demonstrated in the examples given below, when the above method is used in a system that comprises the components described in detail below, it is capable of determining egg fertility on the day that the egg is settled in the incubator with essentially no false positives (that is, every egg identified as fertile is in fact fertile) and fewer than 10% false negatives (that is, <10% of the eggs identified as infertile are actually fertile). The method disclosed herein, when used in a system that composes the components described in detail below, is capable of detecting the sex of a fertile egg with approximately 80% accuracy on the 12th day that the egg is settled in the incubator.

In preferred embodiments of the invention, that is, embodiments in which the detection accuracy is highest, the method disclosed above is performed on an instrument designed and dedicated for measurement and analysis of the spectra of avian eggs according to the disclosed method. Preferred embodiments of the instrument on which the detection method is performed in practice are now described.

In some embodiments of the invention, multiple tests are made substantially simultaneously by using a hyperspectral imaging camera. Such cameras (typically using CCDs as detectors) are well-known in the art, and have the ability to determine light intensity as a function of wavelength and as a function of position of the light source within the camera's field of view. In one exemplary embodiment, each of a plurality of eggs is inserted into an individual sample holder as described below. A plurality of fiber optic cables (at least one per egg) bring the reflected light to the imaging camera, therefore creating a one-to-one relationship between a particular sample holder and the area in the camera's field of view corresponding to that sample holder.

Figure 3:
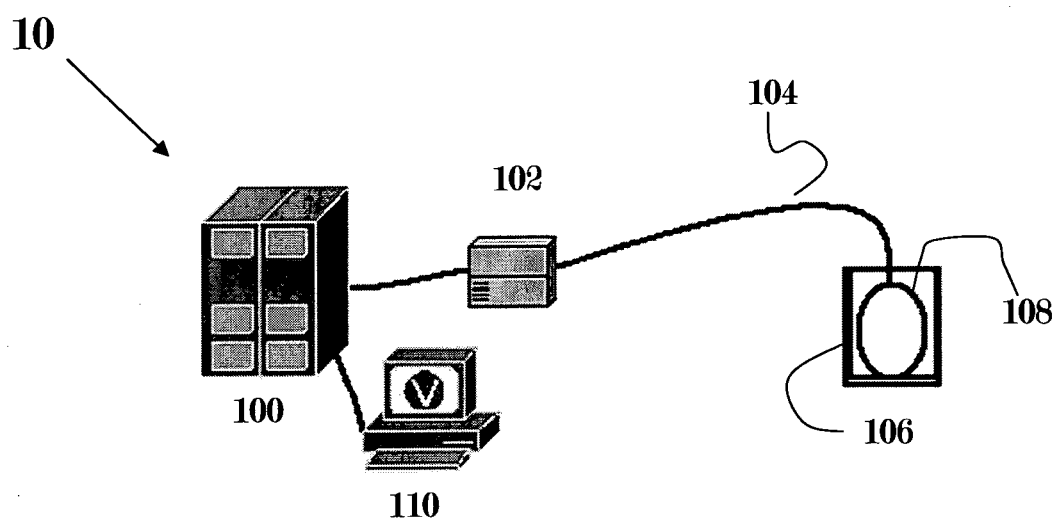
FIG. 3 shows a schematic diagram of an instrument for which spectra are obtained for analysis of avian eggs according to one embodiment of the present invention.

Reference is now made to FIG. 3, which presents a schematic drawing (not to scale) of an embodiment 10 of a spectrometer system on which the spectroscopic measurements discussed above may be made in practice. Spectrometer system 100 provides light source 102 (typically a tungsten-halogen light source, but any light source capable of providing sufficient illumination over the desired wavelength range may be used), optics, at least one detector, mechanical controls of the source, optics, and detector, and means for directing the light to an external target. Light is emitted from the light source; in some embodiments of the invention, the light is brought via fiber optic cable 104 to sample holder 106 in which egg 108 has been introduced. In other embodiments, the light illuminates the egg directly. In preferred embodiments of the invention, sample holder 106 is enclosed in order to prevent interference from stray light. In embodiments in which the sample holder is enclosed, fiber optic cable 104 passes through a hole in one side of sample holder 106. In a preferred embodiment, the hole admitting the fiber optic is located on a side of the box perpendicular to its longest axis and is adapted to admit fiber optic cable 104 such that the cable illuminates the egg substantially along the egg's longitudinal axis. Light reflected from the egg passes back along the fiber optic cable and back into the spectrometer, where it impinges on the detector. Control of the collection of the spectra and storage of the spectra obtained is performed by computer 110. In typical embodiments, multiple measurements are made of each egg introduced into sample holder 106 and then averaged in order to increase the signal-to-noise ratio.

Figure 4A:
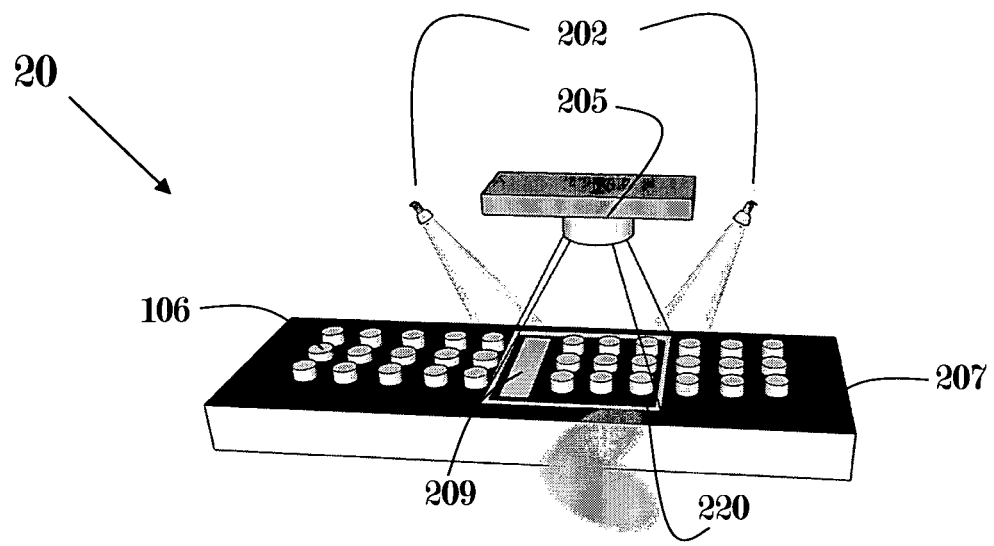
FIG. 4 shows a schematic diagram of an instrument for which spectra are obtained for analysis of avian eggs according to a second embodiment of the present invention.
Figure 4B:
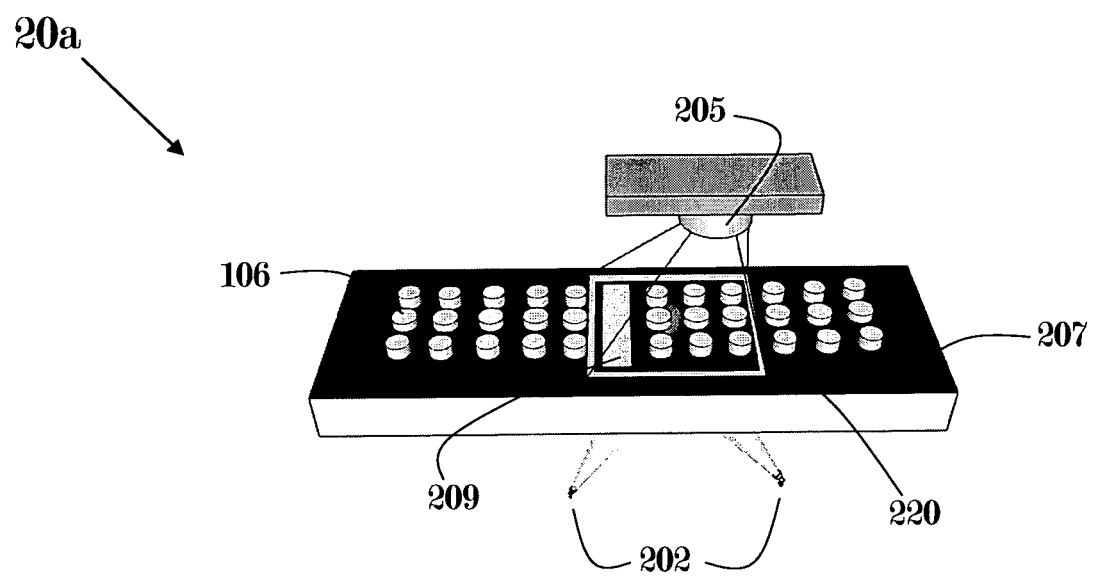

Reference is now made to FIG. 4, which presents a schematic drawing (not to scale) of a second embodiment 20 of a spectrometer system for making the spectroscopic measurements. In this embodiment, spectra of a plurality of eggs 108 are illuminated by light source 202; as illustrated in the figure, in some embodiments, the light source may comprise a plurality of individual lighting elements. At least part of the light emitted from the light source reaches hyperspectral camera 205 after interacting with the eggs. Such hyperspectral cameras are well-known in the art. In embodiments such as the one illustrated in FIG. 4a, the light source and the camera are on the same side of the eggs, in which case, the light reaches the camera after having been at least partially reflected from the egg or eggs being measured, and will hence contain information from which a reflectance spectrum can be constructed. In embodiments such as embodiment 20a illustrated in FIG. 4b, the light source and the camera are substantially on opposite sides of the eggs, and the light from the source reaches the camera only after having at least partially passed through the egg or eggs being measured. In these embodiments, the light reaching the camera will thus contain information from which an absorbance (or, equivalently, transmittance) spectrum can be constructed. In typical embodiments of the device, a spatial resolution of about 0.5 cm is sufficient to obtain the information needed to assess the status of the egg with a sufficiently high signal to noise ratio (SNR). The eggs may be carried past the camera by any means (e.g. a moving belt) known in the art. In order to improve the SNR, background reference spectra are obtained by measuring an appropriate background 207 such as the surface upon which the eggs are placed. Calibration spectra are obtained by measuring the light reaching the camera after interaction with a substance 209 of known spectral properties. A hyperspectral camera snapshot 220 is then obtained of the area within the field of view (FOV) of the camera. Depending on such factors the specific camera being used, the desired spectral and spatial resolution, snapshot 220 may correspond to a measurement of a single egg or to a plurality of eggs within the camera's FOV.

In a preferred embodiment of the invention, a hyperspectral camera is used that can make spectral measurements from the near-UV to the mid-IR. In a most preferred embodiment of the invention, the spectrum is measured from about 300 nm to about 2500 nm.

In some embodiments of the invention, in order to physically locate the egg in space, the method further includes a step of using a spatial filter to measure a predefined area within the camera's FOV, corresponding to a known number of pixels. A measurement is made of the light reaching the camera at a wavelength corresponding to a strong absorption of $CaCO_3$, in a preferred embodiment, about 2340 nm. If a strong decrease in light relative to a background measurement is observed across the pixels, then an egg is known to be within the FOV of the camera, and the spectral measurement is then made.

In preferred embodiments of the invention, the measurements are made while the egg is held in a specially designed dedicated sample holder. Such a holder has the advantage of standardizing the distance from the light source to the egg and from the egg to the detector, as well as keeping the egg in a known location during the measurement.

Figures 5A, 5B:
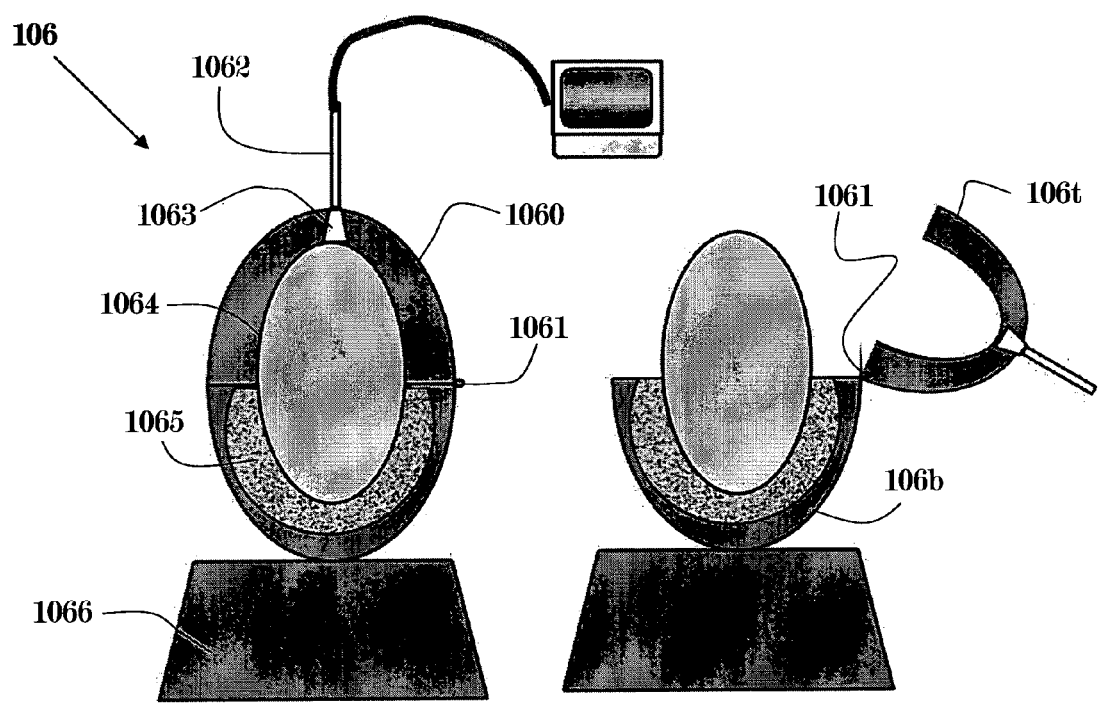
FIG. 5 shows a schematic diagram of one embodiment of a sample holder.

Reference is now made to FIG. 5, which presents a schematic (not to scale) illustration of one embodiment 106 of such a dedicated sample holder. The sample holder can be made of any convenient material that can be made into the requisite shape (e.g. by machining or molding); the material of construction is preferably one that is sufficiently rigid to maintain its shape, to hold an avian egg, and to withstand repeated use without degradation. In a preferred embodiment, sample holder 106 is made of a hard dark plastic. In the embodiment shown in the figure, the sample holder's outer casing 1060 is substantially ovoid. In other embodiments, the outer casing can be of any convenient shape (e.g. cube, parallelepiped, etc.). In the embodiment shown, hinge 1061, located substantially along the equatorial axis of the sample holder, allows the operator to open the sample holder while maintaining the structural integrity of the sample holder. The hinge divides the sample holder into an upper portion 106t and a lower portion 106b. FIG. 5b shows schematically the sample holder in its open position with an egg inserted. The fiber optic cable enters the sample holder via guide tube 1062 and passes through entrance 1063. The guide and entrance are adapted for a slip fit of the fiber optic. The sample holder further comprises an inner surface 1064, which is substantially ovoid and adapted for accepting an avian egg. When the sample holder is in use, the egg being tested contacts at least part of inner surface 1064. In lower portion 106b, the inner surface comprises a soft, dark material 1065, adapted to prevent cracking of the egg and possible reflection of light from internal surfaces of the sample holder when the egg is placed in the sample holder. Soft material 1065 can be any appropriate material (e.g. foam or cotton wool) for holding an avian egg. The hard material out of which the sample holder is made is shaped to accept soft material 1065 such that the entire inner surface (hard material+soft material) essentially defines an ovoid. The sample holder may also optionally include base 1066. Base 1066 is adapted to stabilize the sample holder on a flat surface, and is optionally further adapted for placing the sample holder within a defined area containing a plurality of similar sample holders, for placement on a conveyor belt, etc.

In additional embodiments, the method disclosed herein is adapted for mass production, i.e. rapid analysis of large numbers of eggs substantially simultaneously. In these embodiments, the sample holder will in general be modified from the embodiment illustrated in FIG. 3. In one such embodiment, in place of the hinged arrangement shown in FIG. 3, upper portion 106t is detachable from bottom portion 106b; in embodiments in which the outer casing is, for example, a cube or parallelepiped, upper portion 106t may be a lid. Upper portion 106t is designed to interlock with bottom portion 106b, e.g. by a tab-and-slot system or by having a lip around the perimeter of one half that matches the perimeter of the other half. In these embodiments, upper portion 106t is adapted to be lifted by a remotely controlled device. Such devices are well-known in the art, and are generally adapted for lifting a plurality of objects simultaneously. After the upper portions have been lifted, a second device (of a type well-known in the art) places a plurality of eggs into the sample holders. The top portions are then returned, closing the sample holders, and the spectral measurements made. A separate fiber optic is connected to each sample holder, and the results are measured independently, either in series (one egg at a time, with each spectrum being stored independently in the memory of the computer controlling the apparatus), in parallel (each fiber optic is read by the computer on a separate channel), or both (parallel measurements are made of a portion of the eggs in the sample holders, followed by a second measurement of an additional portion of the eggs, and so on until all of the measurements have been made). After all of the spectral measurements have been made, the upper portions of the sample holders are lifted, the eggs removed and returned to the incubator, and, if desired, an additional set of measurements made. Those eggs that fail to meet a desired criterion (e.g., fertile vs. infertile or male vs. female) can then be discarded.

Reference is now made to FIG. 6, which presents a schematic (not to scale) illustration of a dedicated sample holder 206 according to another embodiment of the invention. The sample holder is contained within casing 2060. The casing may be of metal, plastic, wood, or any other appropriate construction material. In some embodiments of the invention (not shown in FIG. 6), the casing is enclosed on all sides, and includes a door, hinged panel, or other means known in the art for introducing an avian egg; in these embodiments, when the casing is closed, it is light-tight except for the means for the optical connections to the light source and to the spectrometer discussed below. At least one side of the casing contains light admitting means 2063 for introducing light emitted by an external light source 2064. In various embodiments of the invention, the light admitting means may be a hole of appropriate dimensions in the side of the casing, or it may include a window or focusing optics. Within the casing are two substantially parallel support rods 2061, rotatably mounted within the casing and spaced at a distance appropriate for supporting an avian egg and keeping it in optical contact with the light admitting means. The two rods are mechanically connected to at least one motor 2062. In the embodiment illustrated in FIG. 6, a single motor is used to control both rods; in alternative embodiments, each rod is controlled by its own motor.

The motor rotates the two rods about their longitudinal axis, causing the egg placed upon them to rotate while not translating significantly. In a preferred embodiment of the invention, the speed of motor 2062 is controllable (e.g. by an external electronic control apparatus of any type well-known in the art) such that the rate of rotation of the rods may be chosen by the operator. In a most preferred embodiment of the invention, the speed of the motor is chosen such that the egg completes a rotation about once in 13 seconds, during which about 30 spectral measurements are made. The advantage of rotating the egg is that the entire circumference of the egg is thus exposed to the incident light. Not only does this limit the heating of the egg by the external light source, but it enables collection and averaging of multiple spectra of the same egg in order to limit the influence of artifacts that might arise due to inhomogeneities in the egg, in particular in the shell, that might cause a spectrum taken by irradiation of a single spot of the egg to be unrepresentative of the egg as a whole.

The sample holder also comprises means (e.g. a light-tight hole in a side of the casing, or a space on the side of light admitting means 2063) for admitting a fiber optic cable 2064. The other end of the fiber optic cable is in optical contact with a spectrometer as described above. The tip of the fiber optic cable located within the casing is placed in optical contact with the egg such that light can pass from the external light source to the tip of the fiber optic cable and from there to the spectrometer via the egg being analyzed. This setup may be used either in reflectance mode or in transmission/absorbance mode, as described above. In preferred embodiments of the invention, the tip of the fiber optic cable is located 2-4 cm from the egg.

Figure 6A:
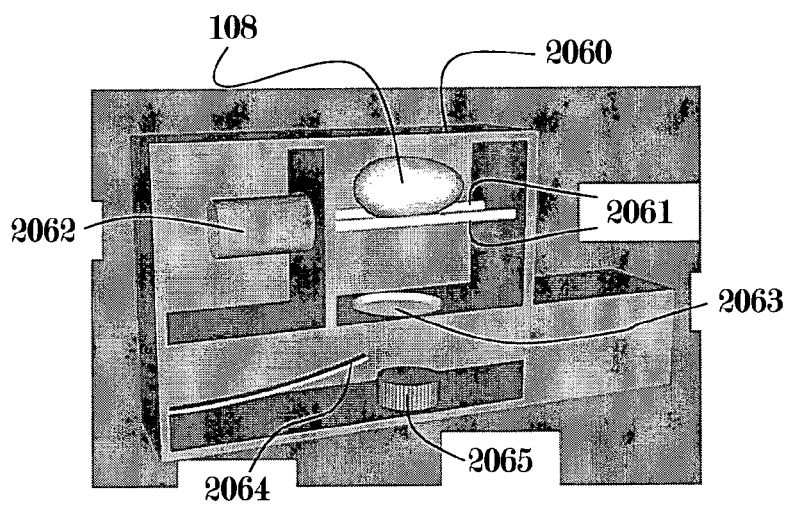
FIG. 6 shows a schematic diagram of a second embodiment of a sample holder.
Figure 6B:
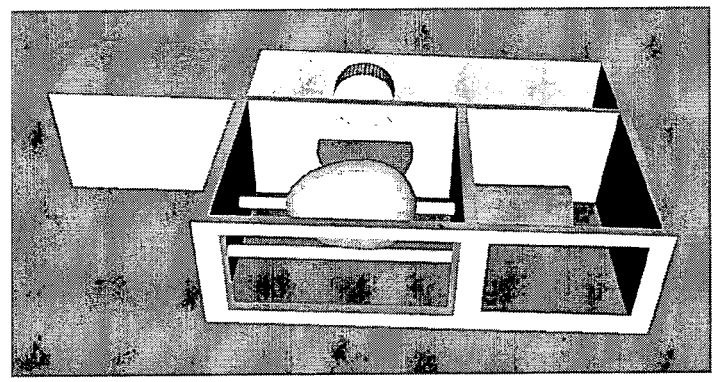
Figure 6C:
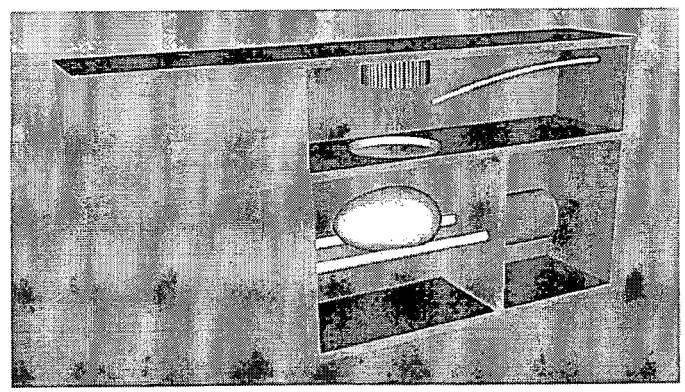

As shown in FIGS. 6a-6c, the light admitting means and means for admitting the fiber optic cable may be on any side of the sample holder relative to the rods supporting the egg. In the embodiment illustrated in FIG. 6a, the rods are located between the egg and the light source, and the light reaches the egg via the space between the rods. In the embodiment illustrated in FIG. 6b, the light admitting means is located such that the light beam is in a plane parallel to that containing the two rods, illuminating the egg from the side relative to the plane upon in which the support rods are located. In a third embodiment, illustrated in FIG. 6c, the light admitting means is located on the side of the egg opposite to that of the two support rods.

In the embodiment shown, each egg to be analyzed is placed individually in the sample holder. In additional embodiments (not illustrated), the device additionally comprises means for automatically introducing the eggs into, and removing them from, the sample holder. Any means known in the art (e.g. a conveyor belt) can be used to perform these tasks.

While the measurements are being made, it is important that the egg not be heated unnecessarily, as overheating the egg may damage it. Different embodiments of the invention include different means for solving this problem. In the simplest method, the light source is held sufficiently far from the egg that the egg is not overheated. The exact distance will depend on the specific optical layout, but in general, it is found that for most embodiments of the invention, the optimal distance from the light source to the egg (that is, the distance that preserves an acceptable SNR while only minimally heating the egg) is found to be about 5-10 cm.

In additional embodiments of the invention, prevention of overheating of the egg is accomplished by controlling the temperature of the environment in which the measurement is made (e.g. within the casing of the sample holder). This temperature control may be active (e.g. thermostatic) or passive (e.g. the sample holder is in thermal contact with a heat bath). In some embodiments of the invention, the sample holder incorporates ventilation means (e.g. on the sides) in order to enable air cooling of the sample holder while measurements are being made.

Example 1

This example demonstrates the use of the invention herein disclosed as a method for determining the fertility of an avian egg on day 0, that is, the day on which the egg is settled in the incubator. In this example, 150 fresh white eggs (White Leghorn breed, Lohmann genetic line) were obtained directly from the henhouse. The fertility of the eggs was determined according to the method disclosed herein and the eggs were then placed in a Peterson incubator at the Faculty of Agriculture of Hebrew University. The eggs were incubated for three days and then opened to determine their fertility. The results of the determination were then compared with the results of the analysis of the measurements that had been made on day 0. The results of the physical check and the results of the analyses were kept separate until the comparison was made. The experiment was repeated several times, including with brown eggs.

From the sample, 50% of the eggs were chosen randomly as the "training" group for the neural network. 25% for validation of the results of the neural network, and the remaining 25% were retained as the test group.

The analysis was performed as follows. First, the spectral data were subjected to a principal components analysis. The five most significant components from each sample were used as the input to the neural network. The Leverberg/Marquand back propagation training function was used. The training of the neural network began with a set of random weights. If after 200 iterations, a suitable set of weights was not found, the training algorithm was begun again with a new set of random weights.

A neural network with three neurons was used, using the "tansig" transfer function in the hidden layer, and the "linear" transfer function for the output layer. The parameters used in the neural network model are summarized in Table 1.

TABLE 1

Neural network parameters for measurement of egg fertility (Day 0)

| IW | | | | | Bias |
|---|---|---|---|---|---|
| 1.470251 | 1.239498 | 2.11928 | −0.22822 | −3.09 | −3.06568 |
| 1.974398 | −4.43216 | −1.65123 | 1.33014 | −0.26772 | −0.50165 |
| 1.050775 | −2.44021 | 1.713201 | −0.40979 | −3.30441 | 1.851835 |

| LW | | | Bias |
|---|---|---|---|
| −3.11852 | −1.83776 | 1.43622 | −1.98368 |
| 3.119206 | 1.53349 | −1.20269 | 2.084955 |

The results of the analysis performed on Day 0 according to the method herein disclosed are compared with the physical determinations made on Day 3 in Table 2.

TABLE 2

Comparison of analysis and physical measurement

| Set | Fertile Spectra Detected | Non Fertile Spectra Detected | Overall Performance |
|---|---|---|---|
| Day 0 Training | 99.5% | 31% | 90.7% |
| Day 0 Validation | 100% | 21.4% | 90.3% |

TABLE 2-continued

Comparison of analysis and physical measurement

| Set | Fertile Spectra Detected | Non Fertile Spectra Detected | Overall Performance |
|---|---|---|---|
| Day 0 Test | 100% | 14.3% | 89.4% |
| Day 0 Overall | 99.7% | 24.6% | 90.2% |

As can be seen in the table, the method disclosed in the present invention successfully detected 99.7% of the eggs that were later determined by physical inspection to be fertile (0.3% false negatives). The method was less successful at identifying infertile eggs on Day 0, only succeeding in identifying 24.6% of the eggs that were later determined by physical inspection to be infertile. Since the ultimate object of the method is to identify and save the fertile eggs, the result can be described alternatively as having successfully identified on Day 0 essentially all of the eggs to be kept in the incubator and nearly a quarter of the eggs that would have to be discarded as infertile. For the eggs investigated in the experiment, the overall success rate was greater than 90%.

Example 2

The same methods were used as in Example 1, except that in this case, the measurement and analysis of the eggs according to the method herein disclosed was performed on Day 1 rather than on Day 0.

The parameters for the neural network model are summarized in Table 3.

TABLE 3

Neural network parameters for measurement of egg fertility (Day 1)

| IW | | | | | Bias |
|---|---|---|---|---|---|
| −1.51573 | 4.826056 | −1.58165 | 1.24418 | −1.88819 | −0.89758 |
| 1.405691 | −3.30712 | −1.15749 | 2.251909 | 1.407275 | −0.78174 |
| −1.13691 | 1.66082 | −2.34412 | 1.886511 | 1.726185 | 1.735988 |

| LW | | | Bias |
|---|---|---|---|
| −2.6754 | −1.93987 | 2.181246 | −0.33096 |
| 2.554909 | 1.968443 | −2.27443 | 0.340324 |

The comparison of the physical determination of the eggs' fertility with the results of the analysis performed according to the method disclosed herein is presented in Table 4.

TABLE 4

Comparison of analysis and physical measurement

| Set | Fertile Spectra Detected | Non Fertile Spectra Detected | Overall Performance |
|---|---|---|---|
| Day 1 Training | 100% | 31% | 91.1% |
| Day 1 Validation | 100% | 42.9% | 92.9% |
| Day 1 Test | 99% | 21.4% | 89.3% |
| Day 1 Overall | 99.7% | 31.6% | 91.1% |

Once again, there was near-perfect detection of the fertile eggs, and of nearly one-third of the infertile eggs, for an overall success rate of 91.1% on Day 1.

Example 3

In this set of experiments, 150 white eggs were obtained from the same source as those used in the previous examples. When the eggs arrived at the henhouse, their fertility was determined, and afterwards, they were placed in the incubator. On the tenth day after the eggs were settled in the incubator, the fertility of the eggs was determined by candling, and on the 12th day, determination of the gender of the chick within each egg was made according to the method disclosed herein. The eggs completed the incubation on the 21st day with their hatching. Upon hatching, the sex of the chick was determined by the method of feather sexing according to procedures well-known in the art. The results of the determination of sex by the physical examination were compared with those of the measurements made on the eggs on the 12th day after they were settled in the incubator.

The principal components analysis and neural network analysis were performed as described above. The parameters of the neural network algorithm are summarized in Table 5.

TABLE 5

Neural network parameters for measurement of chick sex (Day 12)

| IW | | | | | Bias |
|---|---|---|---|---|---|
| −4.64303 | 2.88643 | −1.45288 | 2.267808 | 0.198048 | 4.844547 |
| 1.2139 | 2.66253 | −2.36648 | 2.688683 | 0.955051 | 3.299188 |
| 5.690857 | −0.20077 | −1.18912 | 2.500534 | 0.740264 | 1.993237 |

| LW | | | Bias |
|---|---|---|---|
| 3.03709 | −2.70058 | 1.033565 | −0.67439 |
| −3.03336 | 2.703035 | −1.05007 | 0.669616 |

Table 6 presents the results of the comparison between the results of the measurement and analysis performed according to the method herein disclosed and of the physical determination of sex by the method of feather sexing.

TABLE 6

Comparison of analysis and physical measurement (Day 12)

| Set | Male Spectra Detected | Female Spectra Detected | Overall Performance |
|---|---|---|---|
| Day 12 Training | 86.6% | 68.7% | 79.3% |
| Day 12 Validation | 87.8% | 64.7% | 78.3% |
| Day 12 Test | 87.8% | 52.9% | 73.5% |
| Day 12 Overall | 87.2% | 63.7% | 77.6% |

Nearly 90% of the male chicks were successfully identified as male on Day 12, while nearly two-thirds of the female chicks were successfully identified as female. The overall success rate was 77.6%.

We claim:

1. A non-invasive method for detecting the present condition of an avian egg, comprising the steps of:
    obtaining a test measurement with a hyperspectral camera by measuring, at a predefined portion of a field of view of the hyperspectral camera, an amount of light of at least one predetermined wavelength corresponding to a reflectance or transmittance feature of an avian egg;
    comparing the test measurement to a reference measurement at substantially the same predetermined wavelength;
    confirming presence of an avian egg within the field of view of said camera when a difference between the test measurement and the reference measurement exceeds a predetermined threshold;

obtaining, with the hyperspectral camera, at least one spectrum of the confirmed avian egg over a predetermined wavelength range;

using a neural network algorithm to compare said spectrum with a predefined database of spectra defining possible values of said present condition; and, using the results of said comparison to assess the present condition of said avian egg.

2. The method according to claim 1, further comprising a step of discarding any egg for which said present condition does not match a predefined condition.

3. The method according to claim 1, wherein said step of using a neural network algorithm comprises steps of:

using principal component analysis to transform a data set;

selecting the first m scores from each sample; and, inputting said m scores into a neural network comprising n neurons, a transfer function in a hidden layer, and a linear transfer function for the output.

4. The method according to claim 3, wherein m=5, n=3, and said transfer function in the hidden layer is the "tan sig" function.

5. The method according to claim 1, wherein said step of using a neural network algorithm to compare said spectrum with a predefined database of spectra defining possible values of said present condition further comprises an additional step of preprocessing the spectral data.

6. The method according to claim 5, wherein said additional step of preprocessing the spectral data further comprises a step chosen from the group consisting of (a) performing dimension reduction and (b) performing spectral enhancement.

7. The method of claim 1, further comprising the additional steps of obtaining at least one reference spectrum;

obtaining at least one calibration spectrum;

obtaining at least one test spectrum;

using said at least one reference spectrum to correct said at least one test spectrum; and, using said calibration spectrum to calibrate at least one spectral feature.

8. The method according to claim 7, wherein said step of obtaining a reference spectrum further comprises an additional step chosen from the group consisting of (a) constructing a reference spectrum according to a predetermined physical model and (b) obtaining a reference spectrum by means of physical measurement.

9. The method according to claim 1, wherein said at least one predetermined wavelength is within the calcite absorption band centered at about 2340 nm.

10. The method according to claim 1, further comprising the additional step of placing said avian egg in a sample holder during spectral analysis, said sample holder chosen from the group consisting of:

a sample holder comprising means for excluding ambient light; means for permitting light from a light source to illuminate said egg; and, means for permitting at least a portion of the light reflected from said egg to impinge on a detector; and, a sample holder comprising a casing; two substantially parallel rods rotatably mounted within said casing and arranged to support an avian egg placed thereupon; at least one motor in mechanical connection with said rods, said at least one motor adapted to rotate each of said rods about its longitudinal axis; light admitting means for admitting light emitted by a light source into said casing, said light admitting means disposed such that at least a portion of said light illuminates an avian egg placed upon said rods; and means for admitting one end of a fiber optic cable into said casing such that at least a portion of said light admitted via said light admitting means and reflected from said avian egg enters said fiber optic cable.

11. The method according to claim 1, wherein said present condition is gender, and further wherein said determination is made not more than two weeks after the time said egg is settled in the incubator.

12. The method according to claim 1, wherein said at least one spectrum is chosen from the group consisting of (a) a reflectance spectrum and (b) a transmittance spectrum.

13. The method according to claim 1, wherein said spectrum extends from the near-UV to the mid-IR.

14. The method according to claim 1, wherein said spectrum is a derivative spectrum.

15. An apparatus for non-invasively determining the present condition of at least one avian egg, said apparatus comprising:

a sample holder comprising:

an outer casing operable to exclude ambient light;

an inner casing that defines a test volume;

means for introducing at least one fiber optic cable into the interior of said sample holder; and, means for separating at least part of the upper portion of said sample holder from the lower portion of said sample holder;

a hyperspectral camera configured to capturing a spectrum from an avian egg placed within said sample holder;

data transfer means for transferring said at least one spectrum to a computing device;

computing means installed on said computing device, adapted to analyze said at least one spectrum according to a predetermined algorithm, the algorithm comprising:

obtaining a test measurement captured by the hyperspectral camera, at a predefined portion of a field of view of the hyperspectral camera, of an amount of light of at least one predetermined wavelength corresponding to a reflectance or transmittance feature of an avian egg;

comparing the test measurement to a reference measurement at substantially the same predetermined wavelength;

confirming presence of an avian egg within the field of view when a difference between the test measurement and the reference measurement exceeds a predetermined threshold;

obtaining from the hyperspectral camera at least one spectrum of the confirmed avian egg over a predetermined wavelength range;

using a neural network algorithm to compare said spectrum with a predefined database of spectra defining possible values of said present condition; and, using the results of said comparison to assess the present condition of said avian egg.

16. An apparatus for non-invasively determining the present condition of at least one avian egg, said apparatus comprising:

a sample holder comprising:

a casing;

two substantially parallel rods rotatably mounted within said casing and arranged to support an avian egg placed thereupon;

at least one motor in mechanical connection with said rods, said at least one motor adapted to rotate each of said rods about its longitudinal axis;

light admitting means for admitting light emitted by a light source into said casing, said light admitting means disposed such that at least a portion of said light illuminates an avian egg placed upon said rods; and, means for admitting one end of a fiber optic cable into said casing such that at least a portion of said light admitted via said light admitting means and reflected from said avian egg enters said fiber optic cable, wherein rotation of said avian egg enables collection of spectral data from the entire circumference of said avian egg;

a hyperspectral camera configured to capturing a spectrum from an avian egg placed within said sample holder;

data transfer means for transferring said at least one spectrum to a computing device; and, computing means installed on said computing device, adapted to analyze said at least one spectrum according to a predetermined algorithm, the algorithm comprising:

obtaining a test measurement captured by the hyperspectral camera, at a predefined portion of a field of view of the hyperspectral camera, of an amount of light of at least one predetermined wavelength corresponding to a reflectance or transmittance feature of an avian egg;

comparing the test measurement to a reference measurement at substantially the same predetermined wavelength;

confirming presence of an avian egg within the field of view when a difference between the test measurement and the reference measurement exceeds a predetermined threshold;

obtaining from the hyperspectral camera at least one spectrum of the confirmed avian egg over a predetermined wavelength range;

using a neural network algorithm to compare said spectrum with a predefined database of spectra defining possible values of said present condition; and, using the results of said comparison to assess the present condition of said avian egg.

* * * * *